United States Patent
Hummel et al.

(10) Patent No.: US 10,610,172 B2
(45) Date of Patent: Apr. 7, 2020

(54) IMAGING SYSTEM AND METHOD FOR ENABLING INSTRUMENT GUIDANCE

(71) Applicant: KONINKLIJKE PHILIPS N.V., Eindhoven (NL)

(72) Inventors: Erik Hummel, Eindhoven (NL); Robert Johannes Frederik Homan, Batenburg (NL); Drazenko Babic, Best (NL); Angelique Balguid, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 501 days.

(21) Appl. No.: 14/413,014

(22) PCT Filed: Jul. 11, 2013

(86) PCT No.: PCT/IB2013/055697
§ 371 (c)(1),
(2) Date: Jan. 6, 2015

(87) PCT Pub. No.: WO2014/013393
PCT Pub. Date: Jan. 23, 2014

(65) Prior Publication Data
US 2015/0201892 A1 Jul. 23, 2015

Related U.S. Application Data

(60) Provisional application No. 61/672,368, filed on Jul. 17, 2012.

(51) Int. Cl.
*A61B 6/12* (2006.01)
*G06T 19/00* (2011.01)
(Continued)

(52) U.S. Cl.
CPC .............. *A61B 6/12* (2013.01); *A61B 6/5229* (2013.01); *A61B 6/5247* (2013.01); *A61B 90/37* (2016.02);
(Continued)

(58) Field of Classification Search
CPC ...... A61B 2034/107; A61B 2090/3612; A61B 2090/365; A61B 2090/371;
(Continued)

(56) References Cited

U.S. PATENT DOCUMENTS

| | | | | |
|---|---|---|---|---|
| 2002/0133247 A1* | 9/2002 | Smith | ................ | H04L 29/06 700/94 |
| 2005/0004454 A1* | 1/2005 | Mitschke | ................ | A61B 6/12 600/427 |

(Continued)

FOREIGN PATENT DOCUMENTS

| | | |
|---|---|---|
| EP | 2072012 A1 | 6/2009 |
| WO | 2010067281 A1 | 6/2010 |

OTHER PUBLICATIONS

Navab et al, "Camera Augmented Mobile C-Arm (CAMC): Calibration, Accuracy Study, and Clinical Applications", IEEE Transaction on Meidical Imaging, vol. 29, No. 7, Jul. 2010, pp. 1412-1423.
(Continued)

*Primary Examiner* — Jamie J Atala
*Assistant Examiner* — Joon Kwon

(57) ABSTRACT

Imaging system (100) for enabling instrument guidance in an interventional procedure, comprising: —an input (130) for obtaining an interventional path (220) for use in the interventional procedure, the interventional path being planned based on 3D image data (200) of a patient's interior, and the interventional path being indicative of an entry point (230) on the patient's exterior; —a camera (124-127) for
(Continued)

obtaining a camera image (270) of the patient's exterior during the interventional procedure; —a processor (140) for i) establishing a spatial correspondence between the camera image and the 3D image data, ii) based on the spatial correspondence, calculating a view (280) of the interventional path that corresponds with the camera image, and iii) combining the view of the interventional path with the camera image to obtain a composite image (290); and —a display output (150) for displaying the composite image on a display (162).

19 Claims, 4 Drawing Sheets

(51) Int. Cl.
    *G06F 19/00*     (2018.01)
    *A61B 6/00*     (2006.01)
    *A61B 90/00*     (2016.01)
    *G16H 50/50*     (2018.01)
    *A61B 6/10*     (2006.01)
    *A61B 34/10*     (2016.01)

(52) U.S. Cl.
    CPC ........ *G06F 19/321* (2013.01); *G06F 19/3481* (2013.01); *G06T 19/006* (2013.01); *G16H 50/50* (2018.01); *A61B 6/102* (2013.01); *A61B 6/42* (2013.01); *A61B 6/4441* (2013.01); *A61B 6/466* (2013.01); *A61B 6/582* (2013.01); *A61B 2034/107* (2016.02); *A61B 2090/365* (2016.02); *A61B 2090/3612* (2016.02); *A61B 2090/371* (2016.02); *A61B 2090/376* (2016.02); *A61B 2090/3764* (2016.02); *G06T 2210/41* (2013.01)

(58) Field of Classification Search
    CPC ...... A61B 2090/376; A61B 2090/3764; A61B 6/102; A61B 6/12; A61B 6/42; A61B 6/4441; A61B 6/466; A61B 6/5229; A61B 6/5247; A61B 6/582; A61B 90/37; G06F 19/321; G06F 19/3481; G06F 19/00; G06F 19/3437; G06T 19/006; G06T 2210/41; G16H 50/50
    See application file for complete search history.

(56) References Cited

U.S. PATENT DOCUMENTS

| | | | |
|---|---|---|---|
| 2005/0251030 A1 | 11/2005 | Azar et al. | |
| 2007/0165775 A1* | 7/2007 | Graumann | A61B 6/4441 378/19 |
| 2008/0130836 A1* | 6/2008 | Graumann | A61B 6/06 378/177 |
| 2009/0018701 A1* | 1/2009 | Sattler | A61B 6/102 700/275 |
| 2009/0141958 A1* | 6/2009 | Graumann | A61B 6/02 382/132 |
| 2011/0105895 A1* | 5/2011 | Kornblau | A61B 34/20 600/426 |
| 2011/0257508 A1 | 10/2011 | Feuerlein | |
| 2011/0306986 A1* | 12/2011 | Lee | B25J 9/1689 606/130 |
| 2012/0201449 A1* | 8/2012 | Kim | H04N 13/0018 382/154 |

OTHER PUBLICATIONS

Mitschke et al, "Interventions Under Video-Augmented X-Ray Guidance: Application to Needle Placement", From http://resources.metapress.com/pdf-preview, Mar. 21, 2012, 1 Page Document.

* cited by examiner

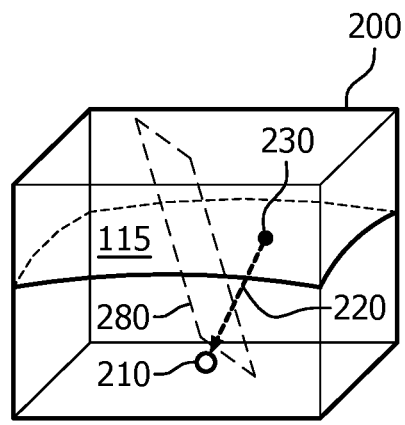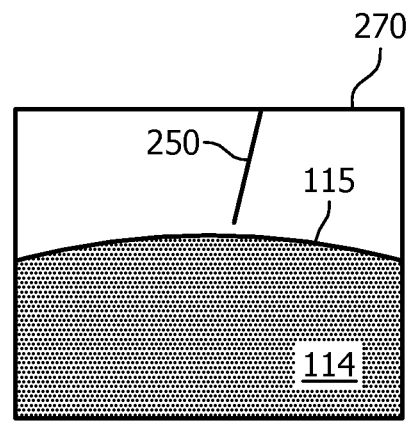
FIG. 2a                FIG. 2b
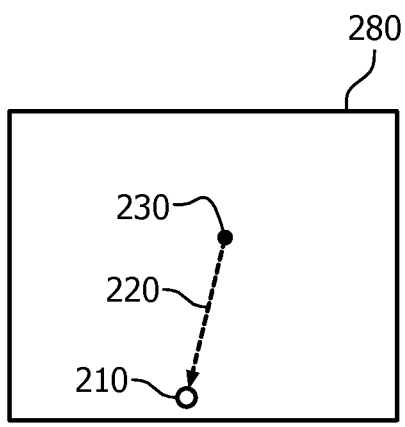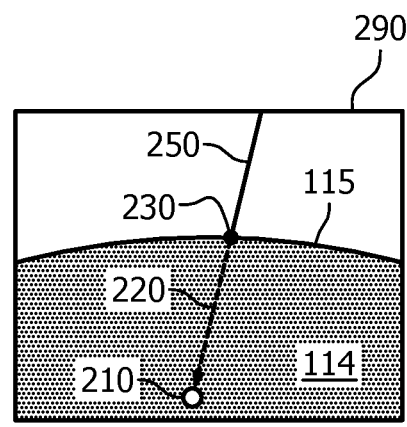
FIG. 2c                FIG. 2d

IMAGING SYSTEM AND METHOD FOR ENABLING INSTRUMENT GUIDANCE

CROSS-REFERENCE TO PRIOR APPLICATIONS

This application is the U.S. National Phase application under 35 U.S.C. § 371 of International Application Serial No. PCT/IB2013/055697, filed on Jul. 11, 2013, which claims the benefit of U.S. Application Ser. No. 61/672,368, filed on Jul. 17, 2012. These applications are hereby incorporated by reference herein.

FIELD OF THE INVENTION

The invention relates to an imaging system for enabling instrument guidance in an interventional procedure. The invention further relates to a method for enabling instrument guidance in an interventional procedure, and to a computer program product comprising instructions for causing a processor system to perform the method.

In interventional procedures, such as surgeries, biopsies, etc, clinicians frequently make use of imaging systems to obtain a view of the patient's interior. For that purpose, imaging modalities such as standard X-ray imaging, Computed Tomography (CT), Magnetic Resonance Imaging (MRI), etc, may be used. The view of the patient's interior may enable the clinician to obtain instrument guidance, i.e., guidance on a position and orientation of an interventional instrument with respect to a target area in the patient's interior, on account of the interventional instrument being visible in the view of the patient's interior. As a result, the clinician may, e.g., determine whether or not, in the course of the interventional procedure, the interventional instrument has deviated from a path towards the target area, and if so, re-position the interventional instrument accordingly.

BACKGROUND OF THE INVENTION

It may be desirable to obtain instrument guidance during an entry phase of the interventional procedure for enabling the clinician to appropriately position and orient the interventional instrument for entry into the patient's interior towards the target area.

A publication titled "*Camera Augmented Mobile C-Arm (CAMC): Calibration, Accuracy Study, and Clinical Applications*", IEEE Transactions on Medical Imaging, Vol. 29, No. 7, July 2010, describes a mobile C-arm which is augmented with a standard video camera and a double mirror system allowing real-time fusion of optical and X-ray images. The video camera is mounted such that its optical center virtually coincides with the C-arm's X-ray source. After a one-time calibration routine, the acquired X-ray and optical images are co-registered. A user interface allows an overlay of the X-ray onto the video image. It is said that the real time image overlay allows the surgeon to easily cut the skin for the instrumentation at the right location, and that it then provides the surgeon with direct feedback during the placement of the surgical instrument.

SUMMARY OF THE INVENTION

A problem of the above system is that it mechanically complex. A further problem of the above system is that it can result in increased radiation exposure.

It would be advantageous to have a system or method for enabling instrument guidance which is less mechanically complex and/or minimizes radiation exposure.

To better address this concern, a first aspect of the invention provides an imaging system for enabling instrument guidance in an interventional procedure, comprising:

an input for obtaining an interventional path for use in the interventional procedure, the interventional path being planned based on 3D image data of a patient's interior, and the interventional path being indicative of an entry point on the patient's exterior;

a camera for obtaining a camera image of the patient's exterior during the interventional procedure;

a processor for i) establishing a spatial correspondence between the camera image and the 3D image data, ii) based on the spatial correspondence, calculating a view of the interventional path that corresponds with the camera image, and iii) combining the view of the interventional path with the camera image to obtain a composite image; and a display output for displaying the composite image on a display.

In a further aspect of the invention, a method is provided for enabling instrument guidance in an interventional procedure, comprising:

obtaining an interventional path for use in the interventional procedure, the interventional path being planned based on 3D image data of a patient's interior, and the interventional path being indicative of an entry point on the patient's exterior;

obtaining a camera image of the patient's exterior during the interventional procedure;

i) establishing a spatial correspondence between the camera image and the 3D image data, ii) based on the spatial correspondence, calculating a view of the interventional path that corresponds with the camera image, and iii) combining the view of the interventional path with the camera image to obtain a composite image; and displaying the composite image on a display.

In a further aspect of the invention, a computer program product is provided comprising instructions for causing a processor system to perform the method set forth.

The above measures enable instrument guidance in an interventional procedure. For that purpose, the imaging system comprises an input which obtains an interventional path for use in the interventional procedure. Here, the term interventional procedure refers to a procedure which involves inserting an interventional instrument into the patient's interior to reach a target area. The interventional path indicates how to reach the target area inside the patient's interior from the exterior of the patient. The interventional instrument may be a small interventional instrument, e.g., a needle, and the clinician may reach the target area by following the interventional path with the needle.

The interventional path has been planned based on 3D image data of the patient's interior. The 3D image data itself is data of the patient's interior which was available when planning the interventional procedure. The 3D image data is of the same patient as is subject to the interventional procedure. The interventional path is obtained in the form of data, e.g., a list of coordinates. The interventional path may also be defined with respect to the 3D image data, e.g., having coordinates in a same coordinate system.

The interventional path is indicative of an entry point on the patient's exterior, i.e., a location on the patient's exterior where the interventional instrument is to be inserted in order to follow the interventional path. The entry point typically corresponds to one end of the interventional path, with the interventional path onwards leading to the target area.

The imaging system further comprises a camera for obtaining a camera image of the patient's exterior during the interventional procedure. A camera is a device which typically comprises a sensor which is sensitive to light, i.e., electromagnetic radiation which is visually perceptible. The camera image shows at least part of the patient's exterior during the interventional procedure. Consequently, the camera image also shows the clinician's hand(s) and the interventional instrument when said instrument is positioned near the part of the patient's exterior. The camera image may be an image from a stream of camera images, e.g., from a video sequence as captured by the camera during the interventional procedure. The camera may therefore be arranged for providing a stream of camera images in real-time or near real-time. Alternatively, the camera may be arranged for obtaining a single camera image or a plurality of camera images at fixed or dynamic intervals.

The system further comprises a processor for establishing a spatial correspondence between the camera image and the 3D image data. Here, the term spatial correspondence refers to data which allows determining how the camera image can be geometrically matched to the 3D image data and/or vice versa. This can be explained as follows. The camera image shows a part of the patient from an exterior perspective. The 3D image data shows a part of the patient from an interior perspective. Geometrically matching involves determining how the part of the patient shown from the exterior perspective can be overlaid, adjoined or in another way spatially corresponding to the part of the patient shown from the interior perspective, and/or vice versa. Based on the spatial correspondence, the processor calculates a view of the interventional path that corresponds with the camera image. As a result, the interventional path is depicted such that it geometrically matches the camera image. Calculating the view may involve, e.g., projecting the interventional path using suitable projection parameters, intersecting the interventional path, etc. As a result, the view shows the interventional path geometrically matching the camera image.

The processor combines the view of the interventional path with the camera image to obtain the composite image. Combining may involve overlaying, fusing, etc. the view with the camera image. As a result, a composite image is obtained which typically shows at least part of the camera image as well as at least part of the view of the interventional path. The system further comprises a display output for displaying the composite image on a display so as to provide the composite image to the clinician.

The inventors have recognized that combining a camera image of a patient's exterior with spatially corresponding information about the patient's interior is advantageous for enabling the clinician to appropriate position and orient the interventional instrument with respect to an entry point on the patient's exterior. At the same time, it is desirable to maintain flexibility in what is shown in the camera image, i.e., the clinician may desire to reposition the camera so as to obtain a better view of the entry point in the camera image. By obtaining an interventional path for use in an interventional procedure, relevant information is obtained which is indicative of the entry point with respect to the patient's interior. By establishing the spatial correspondence between the camera image and the 3D image data which served for planning the interventional path, a view of the interventional path can be calculated that corresponds with the particular camera image. By displaying the view of the interventional path combined with the camera image, the clinician can conveniently determine the position and orientation of the interventional instrument with respect to the entry point on the patient's exterior and the subsequent interventional path inside the patient's interior.

Advantageously, it is not needed to obtain a different view of the patient's interior, e.g., by acquiring a new 2D X-Ray image, with each different camera image, e.g., due to a repositioning of the camera. Advantageously, additional radiation exposure, which would otherwise occur when acquiring a new 2D X-Ray image, is avoided. Rather, use is made of already acquired 3D image data. Advantageously, it is not needed to physically align the camera with an imaging acquisition point since the spatial correspondence between the camera image and the interventional path is calculated based on the 3D image data. Advantageously, a complex mechanical construction, e.g., using mirrors to obtain an optical correspondence between the camera and the imaging acquisition point, is avoided.

Optionally, the imaging system is an X-ray system comprising a C-arm, and the camera is affixed to the C-arm. A C-arm allows repositioning of an X-ray acquisition point with respect to the patient, e.g., to obtain a different view of the patient's interior. By affixing the camera to the C-arm, the same mechanism for repositioning can be also used to reposition the camera, e.g., to obtain a different view of the patient's exterior. Advantageously, the position of the camera with respect to the patient can be easily derived from the position of the C-arm, enabling the spatial correspondence between the camera image and the 3D image data to be more accurately established.

Optionally, the C-arm comprises an X-ray detector, and the camera is arranged alongside or in the X-ray detector. By affixing the camera on the C-arm alongside or in the X-ray detector instead of, e.g., to the X-ray collimator, more working space is available for the clinician when repositioning the C-arm to obtain a typical view of the patient's exterior in the camera image. Advantageously, the camera affixed alongside the X-ray detector does affect the X-ray imaging since it is outside the range of the X-ray beams.

Optionally, the X-ray detector comprises collision sensors arranged along a perimeter of the X-ray detector, and the camera is arranged in a gap between two of the collision sensors along the perimeter. A gap between the collision sensors is well suitable for arranging the camera since this does not increase the outer dimensions of the X-ray detector.

Optionally, the processor is arranged for, upon a re-positioning of the C-arm, i) re-establishing the spatial correspondence between the camera image and the 3D image data, and ii) re-calculating the view of the interventional path that corresponds with the camera image. As such, if the camera obtains a new camera image as a result of the camera being re-positioned through the re-positioning of the C-arm with respect to the patient, said view is automatically re-calculated to match the new camera image.

Optionally, the imaging system comprises a further camera for obtaining a further camera image, the further camera image providing a different perspective of the patient's exterior than the camera image, and wherein:

the processor is arranged for i) establishing a further spatial correspondence between the further camera image and the 3D image data, ii) based on the further spatial correspondence, calculating a further view of the interventional path that corresponds with the further camera image, and iii) combining the further view of the interventional path with the further camera image to obtain a further composite image; and wherein the display output is arranged for displaying the further composite image simultaneously with the composite image.

Therefore, two composite images are displayed, each providing a different perspective of the patient's exterior and each providing a corresponding view of the interventional path. Advantageously, the clinician is provided with a better visualization of the entry point since it is easier to interpret the spatial position of the entry point when viewing the entry point on two different composite images. Advantageously, the clinician can better position the instrument or electromagnetic radiation with respect to the entry point.

Optionally, the imaging system comprises:
a plurality of more than two cameras;
a user input for enabling the clinician to select the camera and the further camera amongst the plurality of more than two cameras.

By selecting the camera and the further camera amongst a plurality of more than two cameras, the clinician can select the best perspectives of the patient's exterior. Advantageously, when the entry point is occluded in the camera image of one or more of the plurality of cameras, e.g., due to the presence of the instrument, the clinician can conveniently select cameras in which the entry point is not, or to a lesser degree, occluded.

Optionally, the processor is arranged for i) based on the spatial correspondence, calculating a view of the 3D image data that corresponds with the camera image, and ii) combining the view of the 3D image data, the view of the interventional path, and the camera image into the composite image.

By additionally showing a view of the 3D image data, the clinician is provided with additional information on the patient's interior which spatially corresponds to the view of the interventional path and the patient's exterior shown in the camera image.

Optionally, the imaging system is arranged for establishing the 3D image data in a pre-interventional imaging procedure of the patient. Since already existing 3D image data is used, it is not needed to additionally acquire image data of the patient's interior. Therefore, radiation exposure of the patient and clinician is kept to a minimum.

Optionally, the 3D image data is of a different modality than a modality provided by the imaging system. For example, the 3D image data may be acquired by MRI, whereas the imaging system is an X-ray imaging system.

Optionally, the spatial correspondence is between a position of the patient in the camera image and the position of the patient in the 3D image data, and the processor is arranged for establishing the position of the patient in the camera image by analyzing the camera image. Changes in the position of the patient are therefore taken into account.

Optionally, the camera is rigidly affixed to the imaging system. A rigid affixation enables the spatial correspondence between the camera image and the 3D image data to be easily and/or accurately established.

Optionally, the processor is arranged for establishing the spatial correspondence based on spatial correspondence data obtained during a calibration phase of the imaging system, the calibration phase comprising establishing a relative position between the camera and the imaging system. Since the camera is part of the imaging system, the relative position between the camera and the imaging system is known or can be determined to a certain degree. By establishing their relative position during a calibration phase, said relative position can be taken into account so as to allow the spatial correspondence between the camera image and the 3D image data to be more easily and/or accurately established. Advantageously, in case the camera is rigidly affixed to the imaging system, the relative position between the camera and the imaging system is fixed throughout various interventional procedures, and therefore, a single calibration phase suffices, i.e., it is not needed to update the spatial correspondence continuously during and/or between interventions for changes in the relative position between the camera and the imaging system. Rather, it is only needed to update the spatial correspondence for changes in the relative position between the camera and the patient, which may be obtained from, e.g., position information of a C-arm in case the camera is affixed to a C-arm of an X-ray imaging system.

It will be appreciated by those skilled in the art that two or more of the above-mentioned embodiments, implementations, and/or aspects of the invention may be combined in any way deemed useful.

Modifications and variations of the method and/or the computer program product, which correspond to the described modifications and variations of the system, can be carried out by a person skilled in the art on the basis of the present description.

A person skilled in the art will appreciate that the method may be applied to multi-dimensional image data, e.g. to two-dimensional (2-D), three-dimensional (3-D) or four-dimensional (4-D) image data. A dimension of the multi-dimensional image data may relate to time. For example, a three-dimensional image may comprise a time domain series of two-dimensional images. The image data may correspond to a medical image, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

FIG. 2a shows 3D image data of a patient's interior and an interventional path that is planned based on the 3D image data;

FIG. 2b shows a camera image of a patient's exterior and an interventional instrument positioned for entry into the patient's interior;

FIG. 2c shows a view of the interventional path that corresponds with the camera image;

FIG. 2d shows the view of the interventional path and the camera image being combined into a composite image;

DETAILED DESCRIPTION OF EMBODIMENTS

In the following, the imaging system is, by way of example, chosen to be an X-ray imaging system. It will be appreciated, however, that the present invention is equally applicable to other types of imaging systems, e.g., MRI, CT, PET, etc.

Figure 1:
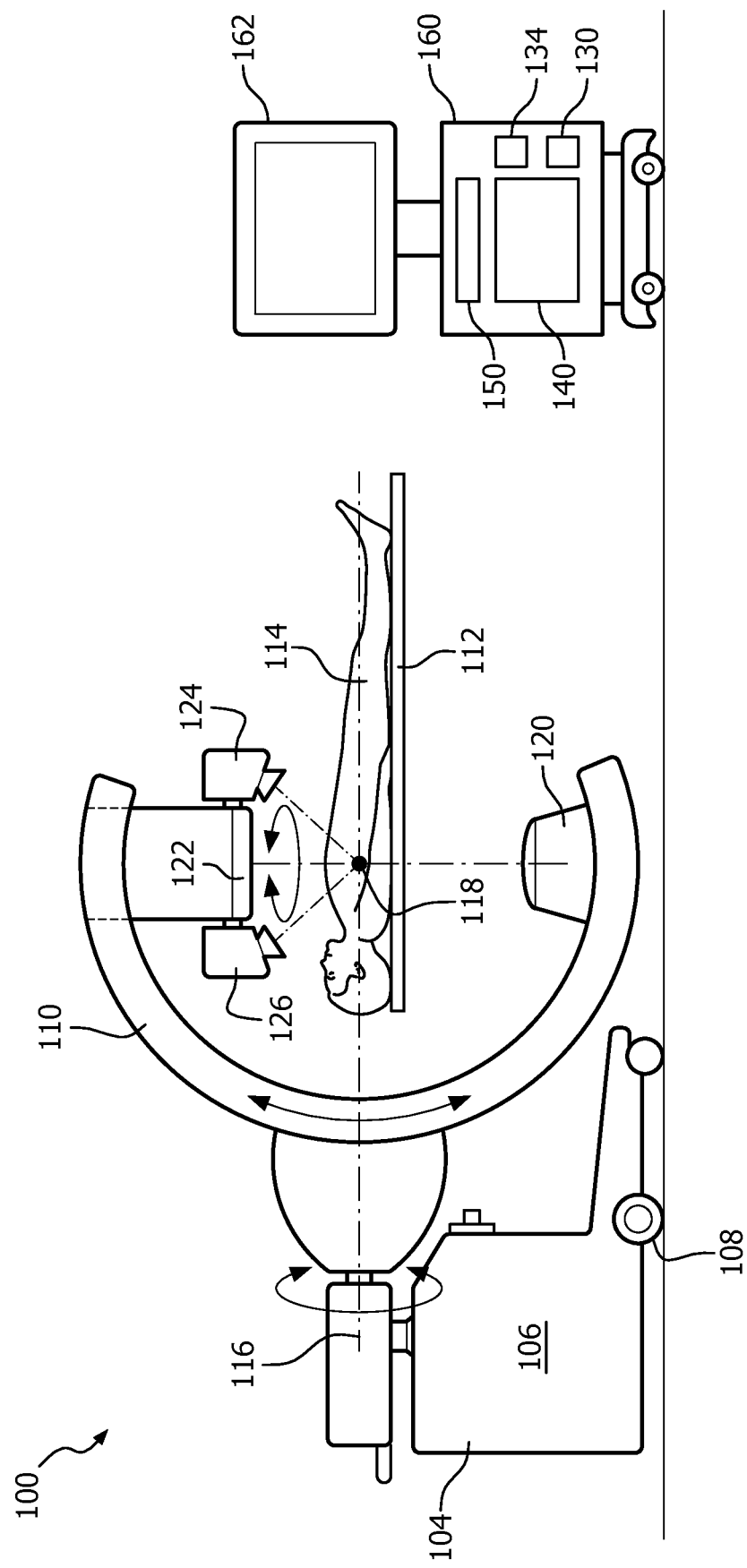
FIG. 1 shows an imaging system according to the present invention.

FIG. 1 shows an X-ray imaging system 100 comprising an X-ray device 104 for providing an X-ray image of a patient's interior. The X-ray device 104 comprises a base frame 106 supported by wheels 108, a C-arm 110 and a surgical table 112 for supporting a patient 114. In this particular example, the patient 114 is shown to be a human patient. The C-arm 110 is rotatable with respect to a first axis 116 being oriented along a main orientation of the surgical table 112. The C-arm 110 is further rotatable with respect to a second axis 118 which is perpendicular to the first axis 116 and parallel to the surgical table 112. An X-ray source 120 and an X-ray detector 122, shown to be a rectangular and flat detector, are mounted on the C-arm 110 such that the X-ray source and the X-ray detector reside opposite one another with respect to the second axis 118.

The X-ray imaging system 100 further comprises a camera 124 for providing a camera image of a patient's exterior. The camera 124 is mounted on the C-arm 110 alongside the X-ray detector 122. In this particular example, the camera 124 is sensitive to wavelengths in the visible spectrum. Moreover, in this example, the X-ray imaging system 100 comprises a further camera 126 which is also mounted on the C-arm 110 alongside the X-ray detector 122, but at an opposite side of the X-ray detector 122. In this respect, it is noted that, unless otherwise noted, the various configurations and uses of the camera 124 which are discussed throughout the specification may also be applicable to the further camera 126.

The X-ray imaging system 100 further comprise an input 130 for obtaining an interventional path, a processor 140 for generating an image, and a display output 150 for displaying the image on a display 162. In this particular example, the input 130, the processor 140 and the display output 150 are shown schematically to be part of a processing unit 160, with the processing unit being part of the X-ray imaging system 100. The processing unit 160 is connected to the display 162 via the display output 150. It will be appreciated, however, that various alternatives are conceivable to the input 130, the processor 140 and the display output 150 being part of a processing unit 160. For example, the input 130, the processor 140 and the display output 150 may be directly integrated into the X-ray device 104.

The operation of the X-ray imaging system 100 may be briefly explained as follows. The input 130 obtains an interventional path for use in an interventional procedure of the patient 114. The camera 140 obtains a camera image 270 of the patient's exterior during the interventional procedure. The processor 140 establishes a spatial correspondence between the camera image and the 3D image data, and based on the spatial correspondence, calculates a view 280 of the interventional path that corresponds with the camera image. The processor 140 combines the view of the interventional path with the camera image to obtain a composite image, and the display output 150 displays the combined image on a display 162.

The operation of the X-ray imaging system 100 may be explained in more detail as follows. FIG. 2*a* schematically shows 3D image data 200 of the patient's interior. Here, a boundary 115 between the patient's interior and exterior is shown. The boundary 115 effectively corresponds to the patient's skin surface, with the patient's interior being located below the boundary 115 and the patient's exterior being located above the boundary 115. FIG. 2*a* further shows a target area 210 of the interventional procedure, and an interventional path 220 leading from an entry point 230 on the boundary 115 towards the target area 230. Typically, the interventional path 220 directly leads towards the target area 210 so as to minimize the extent of the intervention. Hence, the shape of the interventional path 220 typically corresponds to a line. However, other shapes are equally possible. The target area 210 may be identified manually during the path planning, e.g., by the clinician when viewing the 3D image data 200. The target area 210 may also be identified automatically, e.g., using a region-of-interest detector. The interventional path 220 may be planned manually, automatically or semi-automatically before start of the interventional procedure.

It is noted that the input 130 may not need to obtain the 3D image data. For example, the interventional path may be planned using different system, e.g., a workstation, rather than using the X-ray imaging system 100. Moreover, the 3D image data 200 used in planning the interventional path 220 may be of a same modality as the imaging system 100, i.e., 3D X-ray image data. In this case, the 3D image data 200 may be obtained by the X-ray imaging system 100 in a pre-interventional imaging procedure of the patient 114. Alternatively, the 3D image data may be of a different modality, e.g., MRI, CT, PET, etc.

FIG. 2*b* schematically shows a camera image 270 of the patient's exterior. The camera image 270 shows part of the patient 114 as well as the boundary 115 with the background. The camera image 270 may be one of a plurality of camera images. For example, the camera 124 may be arranged for obtaining a video stream of the patient's exterior so as to provide a live view of the patient's exterior on the display 162. The camera image 270 further shows an interventional instrument 250. The interventional instrument 250 may be a needle, scalpel or similar instrument which is used to reach the target area 210. The position of the interventional instrument with respect to the patient 114 may be determined by the clinician, e.g., by the clinician suitably holding the interventional instrument 250.

FIG. 2*c* schematically shows a result of the processor 140 establishing a spatial correspondence between the camera image 270 and the 3D image data 200, and based on the spatial correspondence, calculating a view 280 of the interventional path 280 that corresponds with the camera image 270. The view 280 is also schematically indicated in FIG. 2*a*, and is by way of example chosen to constitute a 2D perspective projection of the interventional path 220. The 2D projection is such that the interventional path 220 is depicted in the view 280 at a position and perspective that matches the patient's exterior in the camera image 270. The view 280 of the interventional path 220 may be generated in the form of a 2D image. However, the interventional path 220 may be depicted such in the 2D image that depth information on the interventional path 220 is included, e.g., by adapting the intensity of the interventional path 220 to a distance to the view 280 in the 3D image data 200. It will be appreciated that the processor 140 may also generate a 3D image of the interventional path 220, e.g., in case the camera 124 is a 3D camera for obtaining a 3D camera image.

It is noted that, instead of a 2D perspective projection, any other suitable technique may be advantageously used to generate a view 280 of the interventional path that corresponds with the camera image 270. It is noted that such techniques are known per se from the technical fields of image processing and image visualization.

Moreover, it is noted that for establishing the spatial correspondence between the camera image 270 and the 3D image data 200, techniques from the technical field of image registration may be used. For example, techniques as described in WO 2010/067281 A1 may be used, which involve using a spatial reference which is detectable in the camera image 270 and in the 3D image data 200 to register the camera image 270 to the 3D image data 200. It is further noted that the camera 124 may rigidly affixed to the imaging system 100, and that this may be used in establishing the spatial correspondence. For example, during a calibration procedure, the field of view of the camera image 270 and the field of view of the 3D image data 200 may be matched so as to establish the spatial correspondence.

Nevertheless, even when the correspondence between the fields of view of the camera image 270 and the 3D image data 200 are known, the patient 114 may be positioned differently with respect to each field of view. Therefore, the spatial correspondence may take into account the difference in position of the patient 114 in the camera image 270 and the position of the patient in the 3D image data 200, e.g., by the processor 140 being arranged for establishing the position of the patient 114 in the camera image 270 by analyzing the camera image and/or the processor 140 being arranged for establishing the position of the patient 114 in the 3D image data 200 by analyzing the 3D image data.

FIG. 2d shows the view 280 of the interventional path 220 and the camera image 270 being combined into a composite image 290. Said combining may involve overlaying the view 280 of the interventional path 220 onto the camera image 270, blending said view 280 into the camera image 270, etc. The processor 140 may be arranged for enhancing the visibility of the interventional path 220 so as to highlight the interventional path 220 in the composite image 290. Having generated the composite image 290, the display output 150 outputs the composite image 290 to the display 162 for display to the clinician. The clinician may then appropriately position the interventional instrument 250 so as to reach the entry point by viewing the composite image. For that purpose, the composite image 290 may be one of a series of composite images, e.g., generated by the processor 140 for each new camera image 270 so as to provide the clinician with a real-time 'live' view on the position of the interventional instrument 250 with respect to the entry point 230.

Figure 3B:
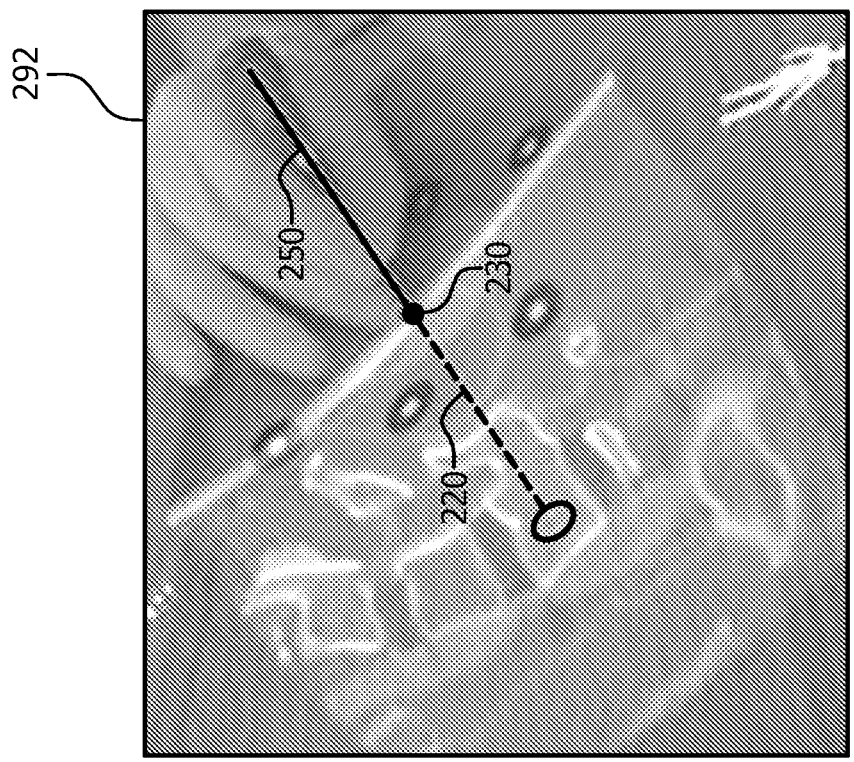
FIG. 3b shows a further composite image based on a further camera, the further camera providing a different perspective on the patient's exterior.
Figure 3A:
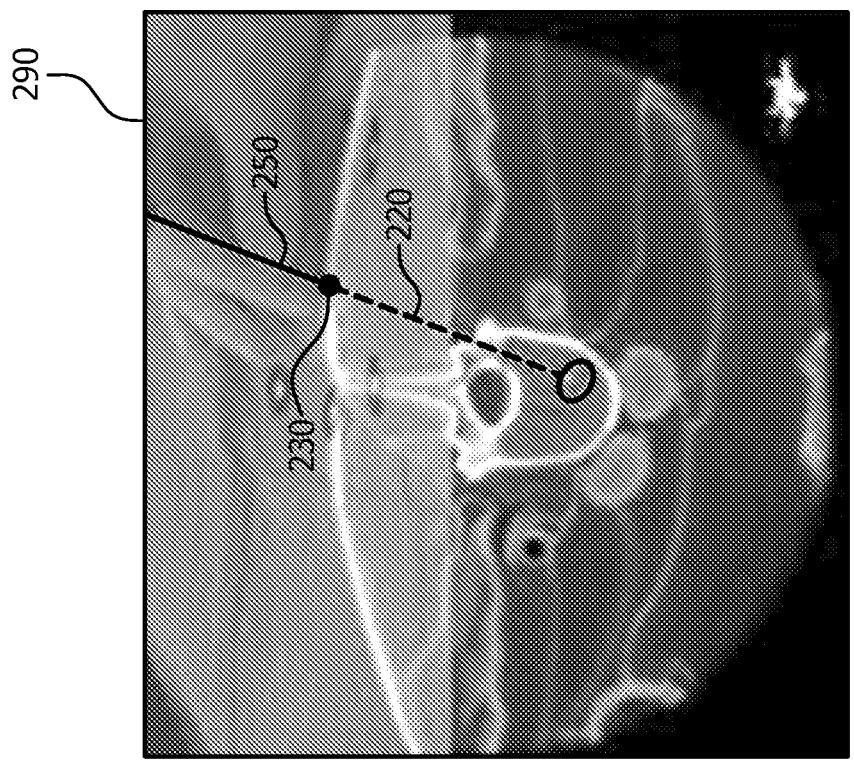
FIG. 3a shows a composite image based on a first camera.

FIGS. 3a and 3b show a result of the imaging system 100 comprising a further camera 126 for obtaining a further camera image, with the further camera image providing a different perspective of the patient's exterior than the camera image. For example, the camera 124, henceforth also referred to as first camera 124, may provide a perspective of the patient's exterior which provides a top-side view of the patient. This view may essentially correspond to a transverse view of the patient yet from the patient's exterior rather than interior. The further camera 126 may provide a perspective of the patient's exterior which provides a side-view of the patient. This view may essentially correspond to a sagittal view of the patient yet from the patient's exterior. However, various other perspectives are possible as well. For example, in the arrangement of the first camera 124 and the further camera 126 as shown in FIG. 1, different frontal perspectives of the patient's exterior are obtained, essentially corresponding to different coronal views from the patient's exterior.

Given the further camera 126, the processor 140 may be arranged for i) establishing a further spatial correspondence between the further camera image and the 3D image data 200, ii) based on the further spatial correspondence, calculating a further view of the interventional path 220 that corresponds with the further camera image, and iii) combining the further view of the interventional path with the further camera image to obtain a further composite image 292. FIG. 3a shows the composite image 290, henceforth also referred to as first composite image 290, and FIG. 3b shows the further composite image 292. The combination of the first composite image 290 and the further composite image 292 allows the clinician to determine the position of the interventional instrument 250 with respect to the entry point 230 and the interventional path 220 from two different perspectives. For that purpose, the display output 150 may be arranged for displaying the first composite image 290 and the further composite image 292 side-by-side on the display 162.

FIG. 3a further shows a result of the processor 140 being arranged for i) based on the spatial correspondence, calculating a view of the 3D image data 200 that corresponds with the camera image 270, and ii) combining the view of the 3D image data, the view 280 of the interventional path, and the camera image into the composite image 290. FIG. 3b shows a same result, yet based on the further camera image obtained from the further camera 126. It can be seen that, in addition to the interventional path 220, details of the patient's interior are visible as well, such as bone segments of the patient's spine. This allows the clinician to verify the position of the interventional instrument 250 with respect to landmarks in the patient's interior, e.g., to verify that critical structures are not affected during entry.

It is noted that although the composite image 290 does not directly provide visual feedback to the clinician on the position of the interventional instrument 250 within the patient's interior after entering the patient's interior through the entry point 23, such feedback is provided indirectly in that the clinician can relatively easily visually extrapolate said position from that of the part of the interventional instrument 250 which is still visible in the camera image 270, i.e., which did not fully enter the patient's interior. Optionally, the imaging system 100 may be arranged for obtaining an image of the patient's interior during the interventional procedure, and the processor 140 may be arranged for including said image in the composite image so as to provide the clinician guidance on the positioning of the interventional instrument 250 after said entering into the patient's interior.

Figure 4:
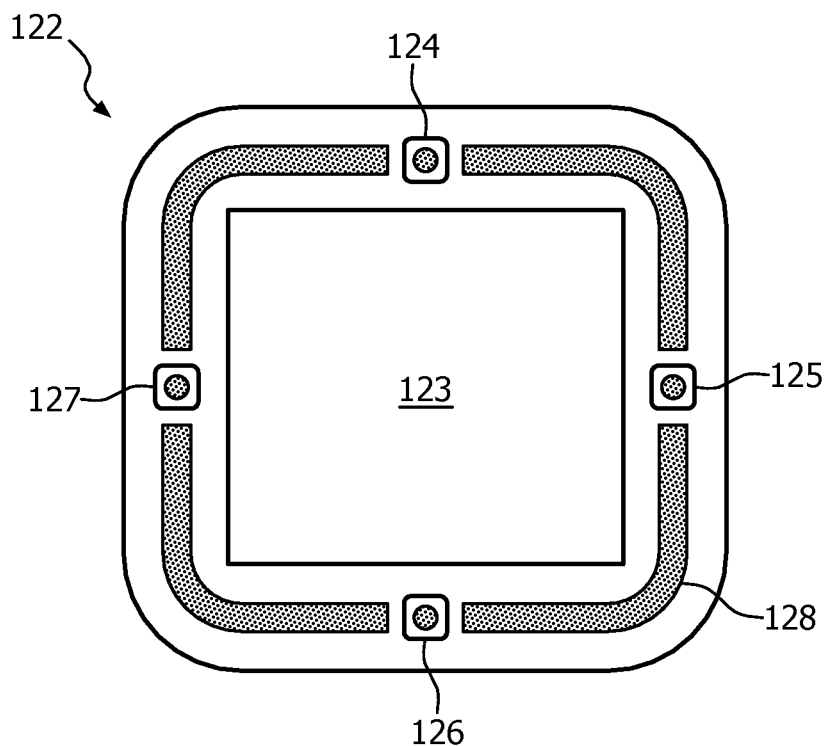
FIG. 4 shows an X-ray detector comprising collision sensors and a plurality of cameras arranged in gaps between the collision sensors.

FIG. 4 shows an optional aspect of the present invention in which the camera 124 is arranged alongside a radiation sensitive surface 123 of the X-ray detector 122. Here, the X-ray detector 122 is a rectangular and flat detector as previously shown in FIG. 1, with FIG. 4 showing a cross-section of the X-ray detector along a main orientation of the detector. Shown centrally within the cross-section of the X-ray detector 122 is the radiation sensitive surface 123. The X-ray detector 122 further comprises a plurality of collision sensors 128 arranged along a perimeter of the X-ray detector 122 and essentially surround the radiation sensitive surface 123. The collision sensors 128 may be arranged for alerting the clinician or operator of the imaging system 100 when the X-ray detector 122 is in close proximity to an object, such as the patient 114, thereby allowing a collision between the X-ray detector 122 and the object to be avoided. The collision may be due to the X-ray detector 122 being moved, e.g., due to be re-positioned as part of a C-arm, and/or the object being moved. FIG. 4 further shows the camera 124 being one of a plurality of cameras 124-127, with each of the cameras being arranged in a gap between two of the collision sensors 128 along the perimeter. Hence, each of the plurality of cameras 124-127 is integrated into the X-ray detector 200, with only the cameras' lenses protruding from the X-ray detector 200 or the X-ray detector 200 comprising openings for the lenses of each of the plurality of cameras.

It is noted that, alternatively to arranging the camera 124 in a gap between two of the collision sensors 128, the camera 124 may in other ways be integrated in the X-ray detector 122. For example, the camera 124 may be a miniature camera, so as to allow a plurality of integration options without needing to increase the size of the X-ray detector 122.

Although not shown in the previous Figs., the processor 140 may be arranged for establishing the spatial correspondence specifically between a position of the patient in the camera image 270 and a position of the patient in the 3D image data 200. For that purpose, the processor 140 may be arranged for establishing the position of the patient in the camera image 270 by analyzing the camera image. For example, the processor 140 may perform patient tracking, e.g., using markers attached to the patient. The position of the patient in the 3D image data 200 may be known, e.g., may have been previously detected. Alternatively, the processor 140 may be arranged for establishing the position of the patient in the 3D image data 200 by analyzing the 3D image data. Hence, a view 280 of the interventional path may be calculated which corresponds with the camera image 270 despite the patient moving during the interventional procedure and thus within the camera image.

In general, in cases where the imaging system 100 comprises a plurality of more than two cameras, e.g., the four cameras as shown in FIG. 4, the imaging system 100 may comprise a user input 134 for enabling the clinician to select the camera 124 and the further camera 126 amongst the plurality of more than two cameras. For that purpose, the user input 134, as is also shown in FIG. 1, may receive selection commands from a user interface means such as a keyboard, computer mouse, touch sensitive surface, etc.

Moreover, in general, the processor 140 may be arranged for, upon a re-positioning of the C-arm 110, i) re-establishing the spatial correspondence between the camera image 270 and the 3D image data 200, and ii) re-calculating the view 280 of the interventional path 220 that corresponds with the camera image 270. It will be appreciated that in general, the present invention may be used to avoid increased radiation exposure which may be a result of the following use of a prior art imaging system. Based on a 3D scan, e.g., using an X-ray modality or any other 3D modality, a path is planned, in principle from the skin of the patient to a region of interest inside the patient. Because of truncation, i.e., due to not the complete 3D scan being available, the path is planned as near as possible to the skin of the patient. A clinical user then positions an X-ray detector of the X-ray imaging system in bulls-eye position, i.e., a position in which a top view of the needle is obtained, by appropriately positioning a C-arm of the X-ray imaging system. The planned path is then projected on live X-ray images. This enables the clinical user to position the needle at an entrance point of the interventional path, with the needling having an appropriate orientation, i.e., facing in the direction of the path. After entry, the clinical user then positions the X-ray detector in a perpendicular view, i.e., being approximately perpendicular to the aforementioned bulls-eye position, again by appropriately positioning the C-arm. The clinical user can then position the needle inside patient with respect to the region of interest based on the planned path projected on the live X-ray images.

The present invention enables the clinical user to position the needle or any other interventional instrument at the entrance point of the interventional path, with the needling having an appropriate orientation, without a need for live X-ray images. Here, the planned interventional path is projected on camera image(s). As such, the clinical user can see his or her hand together with the needle on the camera image(s). The clinical user is thus enabled to place the needle at the entrance point of the interventional path with the needling having an appropriate orientation, i.e., at the 'right' entrance point on the skin of the patient and having the 'right' orientation. Thus, live X-ray images are not needed during this part of the interventional procedure. The clinical user may then continue the interventional procedure by inserting the needle into the patient in the direction of the region of interest.

Moreover, it will be appreciated that, in addition to being less mechanically complex and minimizing radiation exposure, the present invention may enable a shorter workflow for the clinician, i.e., involving less handling, since it is not needed to move the X-ray detector into the bulls-eye position. Advantageously, more working space is available.

The present invention may be used in so-termed minimally invasive percutaneous procedures such as biopsy, ablation, and drainage, in which small interventional instruments are inserted into a patient's interior without separately cutting the patient's skin.

Figure 5:
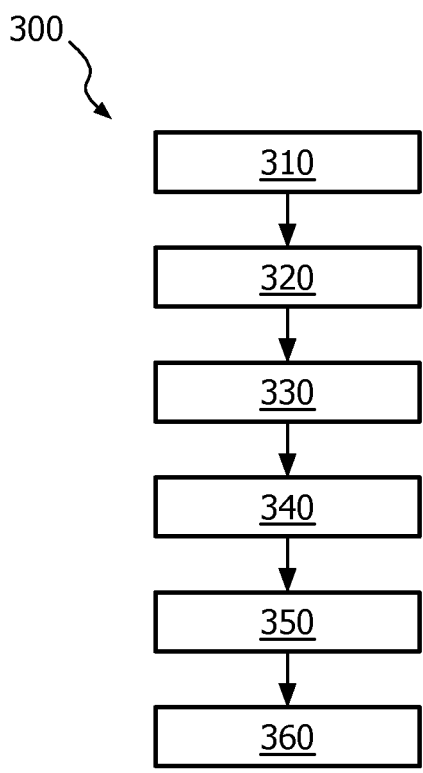
FIG. 5 shows a method according to the present invention.

FIG. 5 shows a method 300 for generating a composite image enabling a clinician to determine an entry point in an interventional procedure. The method 300 comprises a first step titled "OBTAINING INTERVENTIONAL PATH", comprising obtaining 310 an interventional path for use in the interventional procedure, the interventional path being planned based on 3D image data of a patient's interior, and the interventional path being indicative of the entry point. The method 300 further comprises a second step titled "OBTAINING CAMERA IMAGE", comprising obtaining 320 a camera image of the patient's exterior during the interventional procedure. The method 300 further comprises a third step titled "ESTABLISHING SPATIAL CORRESPONDENCE", comprising establishing 330 a spatial correspondence between the camera image and the 3D image data. The method 300 further comprises a fourth step titled "CALCULATING VIEW OF INTERVENTIONAL PATH", based on the spatial correspondence, calculating 340 a view of the interventional path that corresponds with the camera image. The method 300 further comprises a fifth step titled "GENERATING COMPOSITE IMAGE", combining 350 the view of the interventional path with the camera image to obtain the composite image. The method 300 further comprises a sixth step titled "DISPLAYING COMPOSITE IMAGE", comprising displaying 360 the composite image on a display.

The method 300 may correspond to an operation of the imaging system 100. However, it is noted that the method may also be performed in separation of said system.

Figure 6:
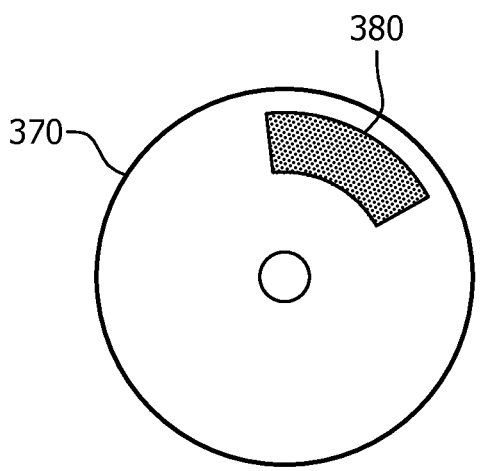
FIG. 6 shows a computer program product according to the present invention.

FIG. 6 shows a computer program product 380 comprising instructions for causing a processor system to perform the method according to the present invention. The computer program product 380 may be comprised on a computer readable medium 370, for example in the form of as a series of machine readable physical marks and/or as a series of elements having different electrical, e.g., magnetic, or optical properties or values.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An imaging system for enabling instrument guidance in an interventional procedure, comprising:
   an input for obtaining an interventional path to be followed by an interventional instrument in the interventional procedure, the interventional path being planned based on three-dimensional (3D) image data of a patient's interior and defining an entry point on the patient's exterior and a target area, and the interventional path being indicative of the entry point on the patient's exterior at which the interventional instrument is to be inserted in order to follow the interventional path;
   a camera for obtaining a camera image of the patient's exterior during the interventional procedure;
   a processor for:
      i) establishing a spatial correspondence between the camera image of the patient's exterior and the 3D image data,
      ii) based on the spatial correspondence, calculating a two-dimensional (2D) perspective projection of the interventional path leading from the entry point on the patient's exterior to the target area that corresponds with a position and perspective that matches the patient's exterior in the camera image, and
      iii) combining the 2D perspective projection of the interventional path with the camera image of the patient's exterior to obtain a composite image; and
   a display output for displaying the composite image on a display.

2. The imaging system according to claim 1, wherein the imaging system is an X-ray system comprising a C-arm, and wherein the camera is affixed to the C-arm.

3. The imaging system according to claim 2, wherein the C-arm comprises an X-ray detector, and wherein the camera is arranged alongside or in the X-ray detector.

4. The imaging system according to claim 3, wherein the X-ray detector comprises collision sensors arranged along a perimeter of the X-ray detector, and wherein the camera is arranged in a gap between two of the collision sensors along the perimeter.

5. The imaging system according to claim 3, wherein the processor is arranged for, upon a re-positioning of the C-arm, i) re-establishing the spatial correspondence between the camera image and the 3D image data, and ii) re-calculating the two-dimensional (2D) perspective projection of the interventional path that corresponds with the camera image.

6. The imaging system according to claim 1, comprising a second camera for obtaining a second camera image providing a different perspective of the patient's exterior than the camera image, and wherein:
   the processor is arranged for i) establishing a second spatial correspondence between the second camera image and the 3D image data, ii) based on the second spatial correspondence, calculating a second two-dimensional (2D) perspective projection of the interventional path that corresponds with the second camera image, and iii) combining the second 2D perspective projection of the interventional path with the second camera image to obtain a second composite image; and wherein
   the display output is arranged for displaying the second composite image simultaneously with the composite image.

7. The imaging system according to claim 6, comprising:
a plurality of cameras; and
a user input for enabling a clinician to select the camera and the second camera amongst the plurality of cameras.

8. The imaging system according to claim 1, wherein the processor is arranged for i) based on the spatial correspondence, calculating a two-dimensional (2D) perspective projection of the 3D image data that corresponds with the camera image, and ii) combining the 2D perspective projection of the 3D image data, the 2D perspective projection of the interventional path, and the camera image into the composite image.

9. The imaging system according to claim 1, arranged for establishing the 3D image data in a pre-interventional imaging procedure of the patient.

10. The imaging system according to claim 1, wherein the 3D image data is of a different modality than a modality provided by the imaging system.

11. The imaging system according to claim 1, wherein the spatial correspondence is between a position of the patient in the camera image and the position of the patient in the 3D image data, and wherein the processor is arranged for establishing the position of the patient in the camera image by analyzing the camera image.

12. The imaging system according to claim 1, wherein the camera is rigidly affixed to the imaging system.

13. The imaging system according to claim 1, wherein the processor is arranged for establishing the spatial correspondence based on spatial correspondence data obtained during a calibration phase of the imaging system, the calibration phase comprising establishing a relative position between the camera and the imaging system.

14. A method for enabling instrument guidance in an interventional procedure, comprising:
planning, on a workstation, an interventional path based on three-dimensional (3D) image data of a patient's interior, the interventional path being indicative of an entry point on the patient's exterior;
obtaining, with an imaging system, the interventional path as planned on the workstation, for use in the interventional procedure;
obtaining a camera image of the patient's exterior during the interventional procedure;
establishing a spatial correspondence between the camera image and the 3D image data;
calculating a two-dimensional (2D) perspective projection of the interventional path leading from entry point to the target area that corresponds with a position and perspective that matches the patient's exterior in the camera image based on the spatial correspondence; and
combining the 2D perspective projection of the interventional path with the camera image to obtain a composite image providing a live view on a position and orientation of an interventional instrument with respect to the planned entry point and the planned interventional path inside the patient's interior; and
displaying the composite image on a display.

15. A non-transitory computer program product comprising instructions for causing a processor system to perform the method according to claim 14.

16. An imaging system for enabling instrument guidance in an interventional procedure, comprising:
an input;
a camera;
a processor; and
a display output;
wherein the input is configured to provide pre-interventional 3D image data of the patient's interior and to provide an interventional path, obtained from a workstation, for use in the interventional procedure, wherein the interventional path has been planned based on pre-interventional 3D image data that shows a part of the patient from an interior perspective, and wherein the interventional path defines an entry point on the patient's exterior where a interventional instrument is to be inserted and a target area within the patient's interior in order to follow the interventional path;
wherein the camera is configured to provide an intra-interventional camera image that shows at least part of the patient's exterior from an exterior perspective during the interventional procedure;
wherein the processor is configured to determine how the intra-interventional camera image and the pre-interventional 3D image data can be geometrically matched in relation to each to other; and wherein the processor is configured to calculate a two-dimensional (2D) perspective projection of the obtained interventional path leading from entry point to the target area that corresponds with a position and perspective that matches the patient's exterior in the camera image such that the interventional path is depicted so that it geometrically matches the camera image, and to combine the 2D perspective projection of the interventional path with the camera image to obtain a composite image providing a live view on a position and orientation of an interventional instrument with respect to the planned entry point and the planned interventional path inside the patient's interior; and
wherein the display output is configured to display the composite image on a display so as to provide the composite image to a user.

17. The imaging system according to claim 1, wherein the processor is further configured to calculate depth information of the interventional path relative to the 2D perspective projection and adapt an intensity of the interventional path in the composite image based on the depth information.

18. The method according to claim 14 further comprising calculating depth information of the interventional path relative to the 2D perspective projection and adapting an intensity of the interventional path in the composite image based on the depth information.

19. The imaging system of claim 1 wherein the imaging system does not include mirrors arranged to establish the spatial correspondence between the camera image of the patient's exterior and the 3D image data.

* * * * *